United States Patent [19]

Mann et al.

[11] Patent Number: 5,020,515

[45] Date of Patent: Jun. 4, 1991

[54] INFLATABLE HAND SPLINT

[75] Inventors: Donaerl B. Mann; David Baras, both of St. Petersburg, Fla.

[73] Assignee: D'Mannco, Inc., St. Petersburg, Fla.

[21] Appl. No.: 612,319

[22] Filed: Nov. 13, 1990

[51] Int. Cl.⁵ ........................... A61H 1/02; A61F 5/04
[52] U.S. Cl. ................................... 128/26; 128/87 R; 128/DIG. 20
[58] Field of Search ................... 128/25, 26, DIG. 20, 128/77, 87 R, 878, 879; 273/54 B, 54 R

[56] References Cited

U.S. PATENT DOCUMENTS

| | | | |
|---|---|---|---|
| 3,217,333 | 11/1965 | Sweet | 128/DIG. 20 |
| 3,457,912 | 1/1967 | Clark | 128/6 |
| 3,581,740 | 6/1971 | Sherbourne | 128/26 |
| 3,937,215 | 2/1976 | Barthlome | 128/DIG. 20 |
| 4,173,218 | 11/1979 | Cronin | 128/DIG. 20 |
| 4,182,320 | 1/1980 | Sweeney | 128/DIG. 20 |
| 4,274,399 | 6/1981 | Mummert | 128/DIG. 20 |
| 4,522,197 | 6/1985 | Hasegawa | 128/25 |
| 4,619,250 | 10/1986 | Hasegawa | 128/25 |
| 4,671,258 | 6/1987 | Barthlome | 128/25 R |
| 4,671,258 | 6/1987 | Barthlomee | 128/25 |
| 4,706,658 | 11/1987 | Cronin | 128/DIG. 20 |
| 4,899,763 | 2/1990 | Sebastian | 128/DIG. 20 |
| 4,907,574 | 3/1990 | Hollerbach | 128/DIG. 20 |

Primary Examiner—Robert A. Hafer
Assistant Examiner—Michael Brown
Attorney, Agent, or Firm—Herbert W. Larson

[57] ABSTRACT

An inflatable hand splint for treatment of patient with arthritic or stroke paralyzed wrists employs a pliable soft vinyl two ply sheet enclosing at a first end an air bladder. The air bladder has an external air valve for attaching to a hand operated air pump. The second end of the soft sheet extends downwardly along the underside of the patient's wrist and is strapped to the patient's forearm with a pair of straps engaged by hook and loop material. A front end of a hard plastic support member is inserted between the fingers and palmer portion of the patient's hand. The rear end of the support member is located below the soft pliable sheet and is also strapped to the patient's forearm. The air bladder is inserted under the patient's finger tips and inflated to move the fingers away from the palmer region.

11 Claims, 2 Drawing Sheets

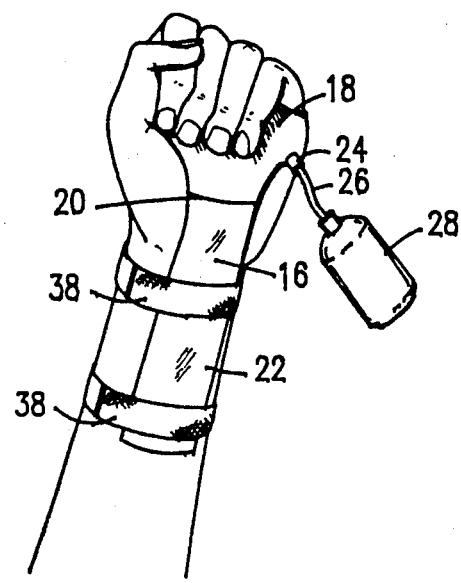
FIG. 1
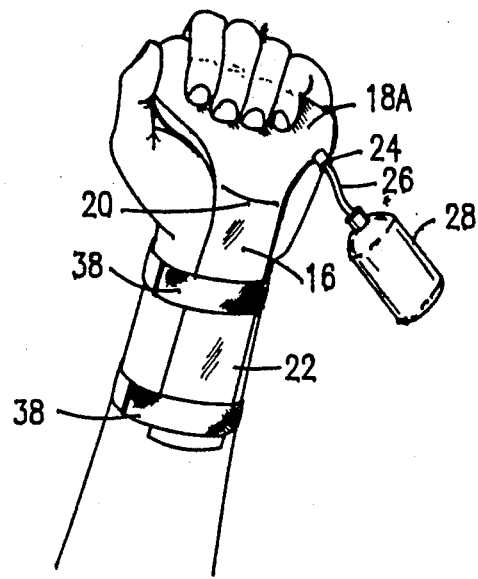
FIG. 2
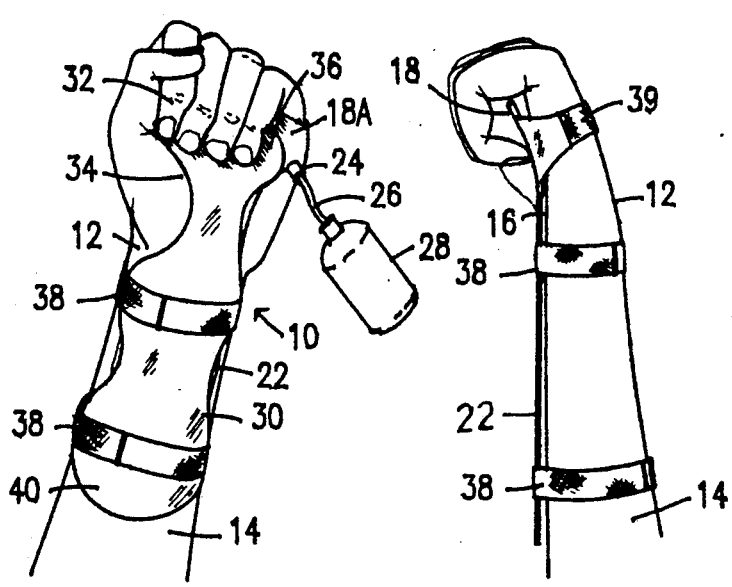
FIG. 3
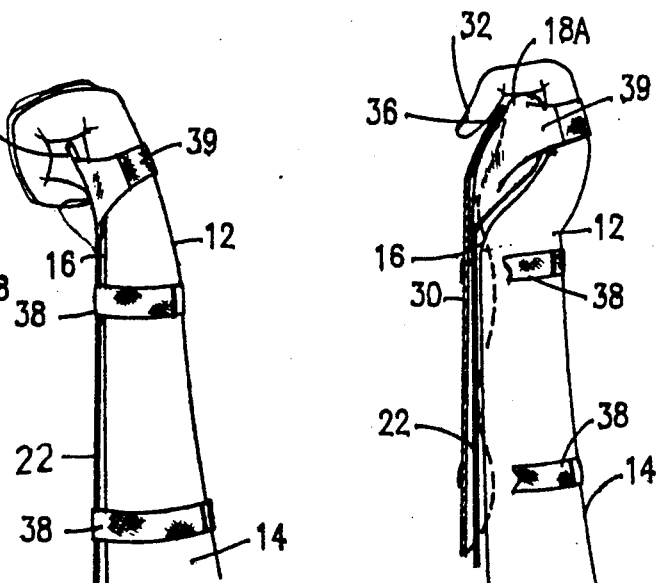
FIG. 4
FIG. 5

INFLATABLE HAND SPLINT

BACKGROUND OF THE INVENTION

1. Field of the Invention

This invention relates to hand splints. More particularly, it refers to an inflatable finger straightening device together with a method for use with stroke victims or other persons suffering from hand paralysis to unbend severely contorted fingers.

2. Description of the Prior Art

Hand splints, such as those shown in U.S. Pat. Nos. 3,938,509 and 4,538,600 are used to correct orthotic conditions or paralytic conditions caused by stroke. These corrective splints assist physical therapists in relieving the effects of a paralyzed hand which tends to turn in towards the wrist and prevents the patient from using his or her fingers. Other patents describe devices for exercising a patient's hand such as U.S. Pat. Nos. 3,457,912; 3,581,740; 3,937,215; 4,274,399; 4,522,197, 4,619,250 and 4,671,258. Although the splints set forth in the above indicated patents are effective for treatment of wrist paralyzed patients and to exercise fingers, a problem frequently occurs in trying to move the fingers away from the palmer region of the hand in stroke victims. The fingers tend to dig into the palm and cannot be forced away if left in that position for long periods of time. An improved hand splint is needed for patients with severely paralyzed wrists to exercise fingers in a direction outward from the palmer region of the hand to prevent fixation of the fingers in an unnatural position.

SUMMARY OF THE INVENTION

I have invented an improved inflatable hand splint device for use on arthritic and stroke patients which is easily applied under the patient's fingers between the finger tips and the palmer region of the hand. By inflating my device the fingers are gently moved outward from the palmer region repeatedly on a scheduled basis to prevent fixation of the fingers in a contorted position.

My inflatable hand splint has a pliable soft vinyl two-ply sheet enclosing at a first end an air bladder. The air bladder has an external air valve for attaching it to a hand operated air pump. The second end extends downwardly along the lower wrist of a patient and is strapped to the patient's wrist with at least two hook and loop wrist bands. The vinyl sheet can have a soft cotton dress enclosing the entire length of the sheet. The deflated first end of the vinyl sheet is gently slipped between the finger tips and palmer region of the patient. The air bladder is gently inflated and deflated to exercise the fingers on a regular schedule. When the finger tips have moved away from the palmer region of the hand a first end of a hard plastic support is slipped under the tips of the fingers exterior to an outer side of the vinyl sheet. The wrist straps hold both the hard plastic and vinyl sheet in place under the wrist and forearm of the patient.

BRIEF DESCRIPTION OF THE DRAWINGS

The invention may be best understood by those having ordinary skill in the art by reference to the following detailed description when considered in conjunction with the accompanying drawings in which:

FIG. 1 is a perspective view of a deflated vinyl sheet of a hand splint of this invention strapped to a patient's forearm.

FIG. 2 is a perspective view of an inflated vinyl sheet of a hand splint of this invention strapped to a patient's forearm.

FIG. 3 is a perspective view of the inflated hand splint with the hard plastic wrist support in place.

FIG. 4 is a left hand left side view of a deflated vinyl sheet positioned between fingers and palm.

FIG. 5 is a left hand, left side partial section view of an inflated vinyl sheet and hard plastic support.

DETAILED DESCRIPTION OF THE INVENTION

Figure 6:
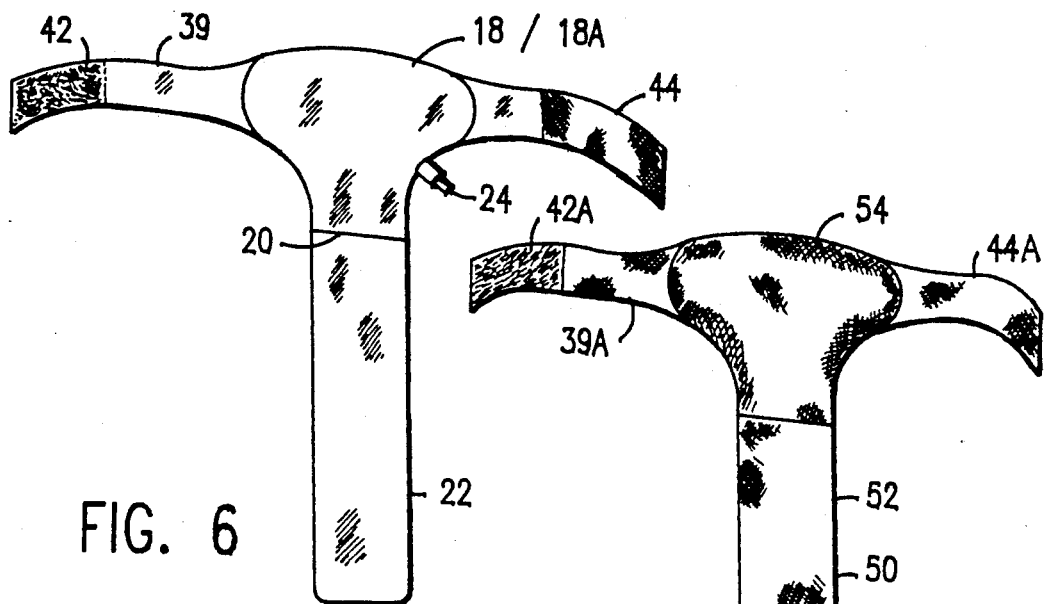
FIG. 6 is a front plan view of the vinyl sheet portion of the hand splint.
Figure 7:
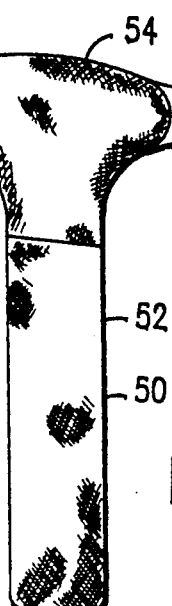
FIG. 7 is a top plan view of a cotton substitute for the vinyl sheet with fabric batting at a top end.

Throughout the following detailed description, the same reference numerals refer to the same elements in all figures.

The inflatable hand splint 10 shown in FIG. 3 is strapped to the lower wrist portion 12 and forearm 14 of a patient. The inflatable hand splint 10 has a soft two-ply vinyl sheet 16 which has a first end 18 enclosing an air bladder which is sealed along seam 20 from the second end 22. An air valve 24 is integral with the first end 18 and is capable of receiving a tube 26 from a small hand held air pump 28. The air pump is usually made from an elastomer or soft plastic. The vinyl sheet 16 is seen in FIG. 1 with the air bladder or first end 18 deflated. In FIG. 2 the first end 18A is inflated by pump 28.

Although the soft sheet 16 is described as being a soft vinyl plastic, it should be appreciated that an elastomer or other soft inflatable material may be substituted for the vinyl plastic.

A hard plastic 30 as seen in FIGS. 3 and 5 is inserted between fingers 32 and the palmer region 34 of a patient after the fingers 32 are partially moved away from the palmer region 34. Only the first end 36 of the hard plastic 30 is slipped under the fingers. The remainder or second end 40 of hard plastic 30 supports the wrist 12 and forearm 14 of the patient. The soft plastic 16 and hard plastic 30 are strapped to the patient as seen in FIG. 3 with at least two hook and loop straps 38. Strap 39 holds the soft vinyl in place over the patient's hand. The straps 38 or 39 can be made of cloth or a plastic and have a hook material 42 at one end and a corresponding loop material 44 at a second end for engagement together around the patient's wrist 12 and forearm 14.

The hard plastic 30 can be made of polyethylene, polypropylene, a polyethylene copolymer or other like substance. It also could be made of wood or metal such as stainless steel or aluminum.

Figure 8:
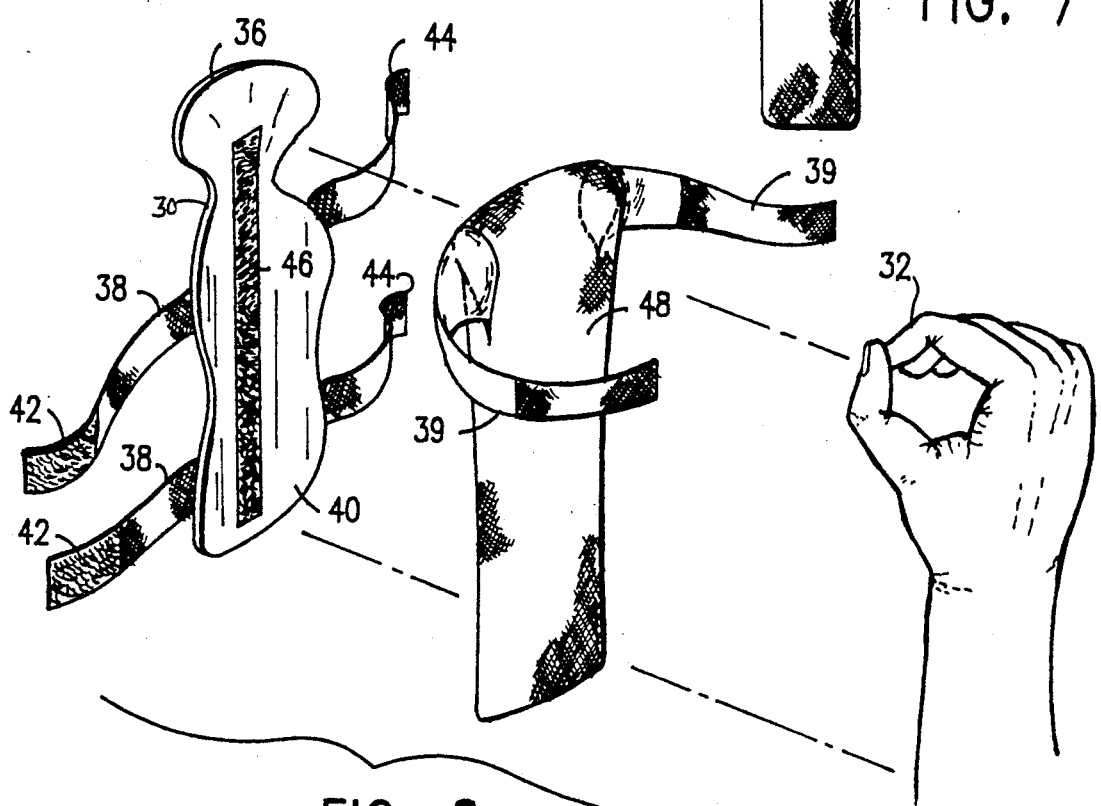
FIG. 8 is an exploded view of the hard plastic wrist support and vinyl sheet with cotton dress positioned for attachment to a patient's wrist.

The inner surface of the hard plastic 30 can have a strip of hook material 46 glued to the plastic as seen in FIG. 8. Additionally, the soft vinyl 16 can have a cotton dress 48 as seen in FIG. 8. This dress provides additional comfort to the patient by absorbing sweat. It can be frequently washed and replaced over the vinyl sheet 16.

After a patient's fingers have been exercised by the inflatable hand splint 10 of this invention so that the fingers do not touch the palmer region any longer, a fabric material 50 can be substituted for the hand splint vinyl sheet 16. This fabric material has a soft fabric batting 54 at a first end and a soft cotton fabric 52 at a second end. Straps 39A with hook and loop material 42A and 44A hold the fabric material 50 in place over the patient's hands. The fabric material 50 is used in the splint for finger stabilization when finger exercise is not being practiced.

Other like materials can be substituted for the materials set forth above to obtain equivalent results.

Having thus described the invention, what is claimed and desired to be secured by Letters Patent is:

1. An inflatable hand splint comprising
   a soft two-ply sheet having an inflatable first end sealed off from a second end, the first end having an air valve connectable to a hand operated air pump to provide a source of air to inflate the first end,
   a pair of connectable strap ends integral with each opposite side of the first end of the soft sheet to tightly attach around a clinched fist,
   a flat stiff sheet substantially conforming in width to a patient's wrist and forearm located in parallel alignment with the soft sheet, at least two straps each having means to connect together at oppositely connecting ends attached to an exterior surface of the stiff sheet and the soft sheet located adjacent an interior surface of the stiff sheet and between the stiff sheet and a wrist and forearm of a patient, the straps being wound around and connected to hold the stiff and soft sheets in position around a forearm of a patient,
   the deflated first end of the soft sheet being located between contorted fingertips and palmer portion of the hand of the patient and the first end of the soft sheet when inflated causing the patient's fingers to move away from the palmer region of the hand.

2. The inflatable hand splint according to claim 1 wherein a soft cloth dress encloses the soft sheet.

3. The inflatable hand splint according to claim 1 wherein the connectable strap ends and means to connect together the straps are corresponding hook or loop material at the ends of each strap.

4. The inflatable hand splint according to claim 1 wherein the soft two-ply sheet and stiff sheet are made from a polymer.

5. The inflatable hand splint according to claim 4 wherein the soft two ply sheet is made from a vinyl polymer and the hard plastic from a polymer selected from the group consisting of polycarbonate, polyethylene, polypropylene and a copolymer thereof.

6. The inflatable hand splint according to claim 1 wherein the first end of the soft sheet has a width substantially the same as the distance betweens the fingers on a hand and the second end is narrower than the width of a patient's wrist.

7. A method of moving contorted fingers of a stroke patient away from the palmer region of the patient's hand comprising
   inserting a first end of a soft two-ply sheet between the fingertips and palmer region of the patient's hand, with a second end of the sheet extending along a lower wrist and forearm of the patient, the first end of the soft sheet having an attached air valve;
   inserting a stem leading to a hand held air pump into the air valve and alternatingly inflating and deflating the first end of the soft sheet to exercise the patient's fingers and move them away from the palmer portion of the patient's hand.

8. The method according to claim 7 wherein a hard sheet is applied to an outer surface of the soft sheet and at least two straps attached to the hard sheet are wrapped around the patient's forearm to retain the hard sheet and soft sheet juxtaposed to an underside of the patient's forearm.

9. The method according to claim 7 wherein a pair of strap ends integral with the opposite side edges of the soft sheet first end are tightly wrapped around the patient's fist and held together by hook and loop material.

10. A method according to claim 7 wherein a soft absorbent cloth dress is draped around the soft sheet.

11. The method according to claim 7 wherein a soft cloth sheet with a batting at a first end is substituted for the soft sheet when the patient's fingers are moved away from the palmer region of the hand.

* * * * *